United States Patent [19]

Smith

[11] Patent Number: 4,649,932
[45] Date of Patent: Mar. 17, 1987

[54] METHOD AND APPARATUS FOR DERIVING CURRENTS AND POTENTIALS REPRESENTATIVE OF THE IMPEDANCES OF ZONES OF A BODY

[75] Inventor: Denis N. Smith, Edinburgh, Scotland

[73] Assignee: National Research Development Corp., London, England

[21] Appl. No.: 600,273

[22] Filed: Apr. 13, 1984

[30] Foreign Application Priority Data

Apr. 13, 1983 [GB] United Kingdom ............... 8309927

[51] Int. Cl.⁴ ............................................. A61B 5/05
[52] U.S. Cl. .................................... 128/734; 128/693
[58] Field of Search ........................... 128/734–735, 128/741, 693, 723, 802, 639, 644; 324/57 R, 62, 65 R; 364/481–482, 415–417

[56] References Cited

U.S. PATENT DOCUMENTS

| | | | |
|---|---|---|---|
| 3,452,743 | 7/1969 | Rieke | 128/734 |
| 3,957,037 | 5/1976 | Fletcher et al. | 128/693 X |
| 4,269,195 | 5/1981 | Itoh | 128/734 X |
| 4,275,743 | 6/1981 | Hjort | 128/644 X |
| 4,300,574 | 11/1981 | Briggs | 128/734 |
| 4,458,694 | 7/1984 | Sollish et al. | 128/734 |
| 4,486,835 | 12/1984 | Bai et al. | 128/734 X |
| 4,539,640 | 9/1985 | Fry et al. | 128/734 X |

FOREIGN PATENT DOCUMENTS 1516417 4/1975 Fed. Rep. of Germany .

OTHER PUBLICATIONS

Henderson; "An Impedance Camera for Spatially Specific Measurements of the Thorax"; *IEEE Trans. on Biomed. Engr.*, vol. BME-25, No. 3, 5-1978, pp. 250–254.

Paper from The Annals of the New York Academy of Sciences, vol. 170 (1970) pp. 532–549, Kenneth Lifshitz, M. D. Orangeburg, New York.

Electrical Impedance Imaging of the Thorax, Yongmin Kim et al, pp. 246–257, Mar. 18, 1983.

An Electrical Resistivity Method for Evaluating the In-Situ Porosity of Clean Marine Sands, pp. 91–114, Peter Douglas Jackson.

Focussed Electrical Resistivity Arrays: Some Theoretical and Practical Experiments, pp. 601–626, 1981; P. D. Jackson.

*Primary Examiner*—Kyle L. Howell
*Assistant Examiner*—Angela D. Sykes
*Attorney, Agent, or Firm*—Cushman, Darby & Cushman

[57] ABSTRACT

In deriving the impedance of a zone of a body errors arise when currents used stray from the zone due to movements of, and/or changes within the body. In the invention a current used for deriving impedance is passed through a zone under investigation using current electrodes outside the zone. A potential also required for deriving impedance is available at two potential sensing electrodes at ends of the zone. The current is confined to the zone by passing control currents just outside the zone between pairs of control current electrodes to set up virtual current barriers minimum along the boundaries of the zone. Pairs of potential sensing electrodes straddling the boundaries are used to adjust currents passed by the control current electrodes to establish the positions of the boundaries and to stabilize these positions when movement and/or internal functional change occurs.

19 Claims, 16 Drawing Figures

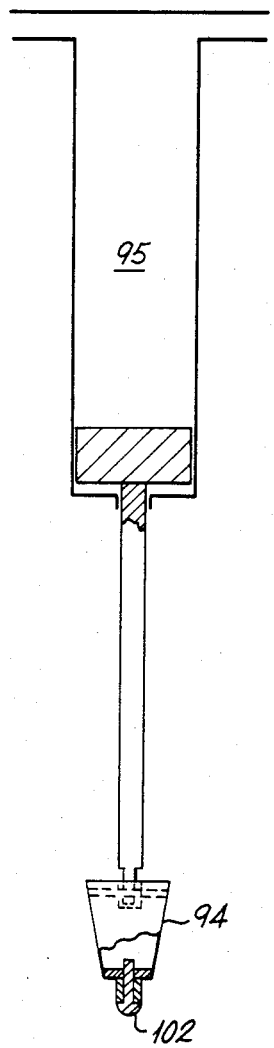
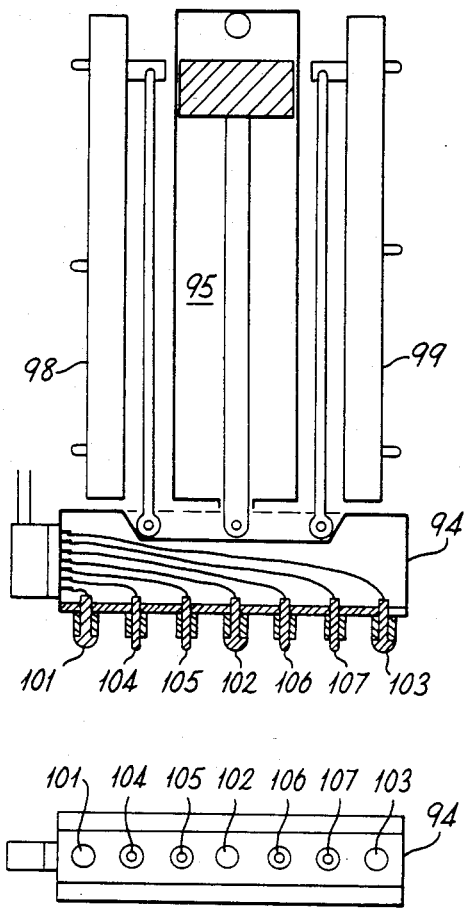

METHOD AND APPARATUS FOR DERIVING CURRENTS AND POTENTIALS REPRESENTATIVE OF THE IMPEDANCES OF ZONES OF A BODY

FIELD OF THE INVENTION

The present invention relates to methods and apparatus for deriving currents and potentials representative of the impedances of zones of a body, and therefore representative of the internal structure of many types of body. The term body is used generally here to mean any finite object but the invention is particularly useful in connection with the animal, especially human, body. Variations in time of the impedance of the zone can also be derived. The invention has particular application in diagnostic cardiology and other branches of investigative medicine.

BACKGROUND OF THE INVENTION

Methods and apparatus for the determination of the impedance of zones of the thorax, head and limbs are known in which a current is passed through the body and potentials in the body are measured. Impedance changes may be recorded which are correlated with the cardiac, respiratory or other functions of the body due to variations in blood, air or other contents of regions of the body. For example by using such apparatus an evaluation of the stroke-volume of the heart, and respiration and perfusion of the lungs may be made.

A fundamental problem which occurs in such known methods is that a current passed into the body tends to diverge from the entry electrode until limited by an external boundary of the body, converging again at an exit electrode. With bodies having an irregular boundary suitable geometrical factors cannot be computed to allow for this boundary and changes in the boundary may be interpreted as changes in the contents of a zone measured. Further, when inhomogeneities are encountered in the body the current tends to converge towards regions of high conductivity and diverge from regions of low conductivity. Current does not therefore flow naturally in straight or even easily described curved paths in an inhomogeneous medium. Changes in the contents of a zone under investigation cause local changes in impedance and therefore in current paths so that any impedance measured changes not only because the contents of the zone change but also because the current flow patterns change.

U.S. Pat. Nos. 2,712,627 to 2,712,630 describe measuring the resistivity of earth formations by lowering electrodes into a borehole. In this method a current sheet perpendicular to the borehole is generated by injecting flanking currents but the sheet diverges so that the resistivities of volumes of material remote from the measuring point and which are irrelevant to the required value become involved in the measurement. Variants of this method are described in "The Microlaterolog" by H. G. Doll in Petroleum Transactions, AIME, Vol. 198, 1953, where the flanking current is injected by a circular electrode concentric with a primary electrode and by Jackson, Marine Geotechnology Vol. 1, no. 2, page 91 at seq. (1975) where the electrodes are grouped into two concentric sets of electrodes of opposite sign which are located on the same insulating pad. With the Microlaterolog the path of the current tube and its cross-section are thought to be modified by variations in conductivity as the electrodes are lowered below the surface; that is as the electrodes are lowered down the borehole and volume of material whose resistivity is measured varies because current patterns vary.

SUMMARY OF THE INVENTION

According to a first aspect of the present invention there is provided medical diagnostic or investigative apparatus for deriving signals representative of the impedance of a zone of an animal body, comprising means for passing first currents between electrodes of a first group suitable for location on at least one surface of an animal body, the electrodes being, in operation, positioned to pass the first currents through a zone whose impedance is to be measured, means for deriving the potential across the zone due to the first currents and in the general direction thereof, means for passing second currents through the body between electrodes of a second group also suitable for location on at least one surface of the body to establish virtual barriers as hereinafter defined generally coinciding with boundaries of the zone within the body, means for deriving from potentials in the body control signals representative of the positions of the said virtual barriers, and means for controlling the second currents in accordance with the control signals to control the positions of the said virtual barriers, the potential across the zone being representative of the impedance of the zone.

The first currents may also be used in providing an indication of the impedance of the zone.

In this specification and claims a "virtual barrier" is a barrier to electrical current formed when there is no potential gradient in a body perpendicular to the barrier and maximum potential gradient along the barrier. The currents on either side of the said virtual barrier originate from and/or proceed to, separate electrodes.

One of the most important advantages of the invention is that obtained when the impedance of a zone of a human body is derived using external electrodes placed on the surface of a body. Even when the contents of the zone vary or the external boundaries of the body change, the virtual barriers localise the zone to allow its impedance to be derived.

Preferably the means for deriving control signals comprise pairs of potential sensing electrodes straddling the virtual barriers. By means of difference amplifiers connected to the potential sensing electrodes, the second currents are controlled so that in each pair the sensing electrodes are at equal potentials and the potential minima defining the barriers are located between the sensing electrodes.

The invention can be applied to measuring the impedance of a plurality of zones simultaneously. By positioning the electrodes round a portion of the body and switching the currents so that they pass in different directions through a segment of the portion, a tomographic image may be formed.

According to a second aspect of the invention, therefore, there is provided apparatus for deriving signals representative of the impedance of a zone of a cross-section of a closed body, comprising an assembly including a supporting member, a plurality of electrode holders mounted thereon, the supporting member being arranged to encircle, in operation, a portion of the body with electrodes held by the holders in contact with the surface thereof, means for passing first currents between a plurality of the electrodes in a first group positioned to pass the first currents through a zone whose impedance is to be measured, means for deriving the potential across the zone due to the first currents and in the general direction thereof, means for passing currents through the body between a plurality of the electrodes in a second group positioned in relation to electrodes of the first group to establish virtual barriers as hereinbefore defined generally coinciding with boundaries of the zone within the body, means for deriving from potentials in the body control signals representative of the positions of the potential barriers, and means for controlling the second currents in accordance with the control signals to control the positions of the potential barriers, the potential across the zone being representative of the impedance of the zone.

The body may be that of an inanimate object such as a pipe or the pillar of a building, or a plant such as a tree trunk, or of an animal particularly a human.

For this purpose a fairly large number of electrodes has to be applied to the skin at the same time and therefore respective piston and cylinder arrangements may be provided for the holders so arranged to cause relative movement between the pistons and cylinders which in one direction press the electrodes on to the skin, when fluid is introduced into the pistons.

According to a third aspect of the present invention there is provided a method of deriving the impedance of a zone of a body using electrodes placed in contact with the body wherein the dimensions of the zone are comparable with the maximum distance between the electrodes, comprising positioning and energising electrodes of a first group on the surface of the body to pass first currents through the zone, deriving the potential across the zone due to the first currents an in the general direction thereof, positioning and energising electrodes of a second group in two regions of the body to establish virtual barriers, as hereinbefore defined, generally coinciding with boundaries of the zone within the body, adjusting the control currents in accordance with potentials representative of the positions of the virtual barriers to control the said positions, and deriving the impedance of the zone from the said potential across the zone.

Another important feature of the invention is the realisation that it can be used for bodies having zones under investigation with dimensions comparable with the maximum distance between electrodes for example approximately equal.

BRIEF DESCRIPTION OF THE DRAWINGS

Certain embodiments of the invention will now be described by way of example with reference to the accompanying drawings, in which.

DETAILED DESCRIPTION OF THE INVENTION

In most applications of the present invention it is required to pass current through a human body. In order to carry out such a procedure it is necessary to restrict the operating currents and frequencies within known safety limits. Consequently it must not be attempted by persons not having a comprehensive knowledge of the consequent effects. As a general guide, but not one which should be followed by persons without the above knowledge, British Standard BS 5724 Part 1, Paragraph 19.3 should be complied with. This allows for a "Patient Auxiliary Current" of up to 0.1 mA (rms) below 1 kHz and 0.1 mA × frequency/$10^3$ up to a maximum of 10 mA (rms) for higher frequencies. Impedance plethysmography is noted as a specific example in the definition of "Patient Auxiliary Currents" (Paragraph 25.4). Typically the circuits described below operate with a nominal 100 μA peak to peak current in each zone (e.g. for FIG. 1 a total of 300 μA peak to peak at 10 kHz and 900 μA peak to peak for FIG. 3) which is well within the allowed limits. In those circuits with a plurality of zones, the total current is subdivided to the additional zones rather than increased in proportion to their number. Of course these considerations do not apply when the body under investigation is inanimate.

Figure 1:
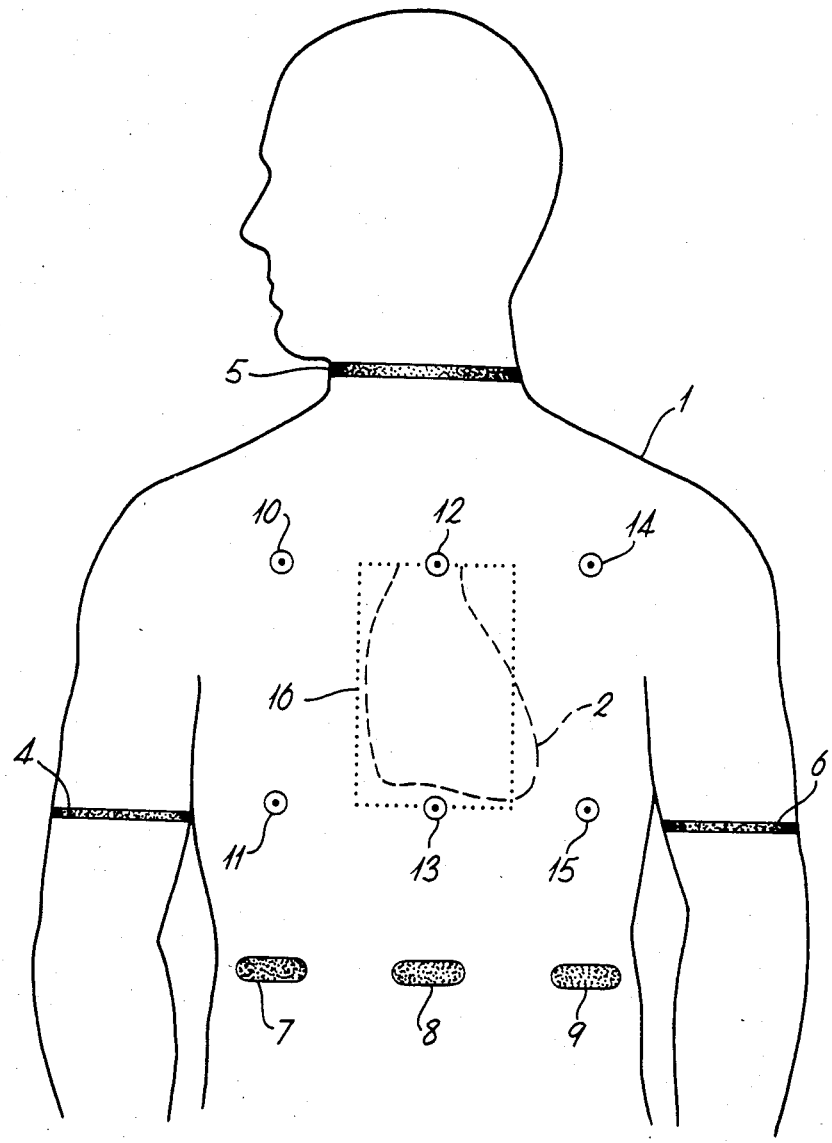
FIG. 1 shows the layout of electrodes for use in determining the impedance and stroke-volume of the heart.

In FIG. 1 the front of the body is represented in outline at 1, with the heart shown by dashed lines at 2. Three current input electrodes 4, 5, 6 are shown as bands applied around the arms and the neck. Additionally three current output electrodes 7, 8, 9 are shown as short strips applied at the waistline. Between the electrodes 4 and 7, 5 and 8, 6 and 9 lie electrode pairs 10 and 11, 12 and 13, and 14 and 15, respectively, for the determination of potential and potential differences. The electrodes 12 and 13 are placed on the left sternal margin just above and below the limits of the heart outline. The electrodes 10 and 14 are equally spaced to the right and the left of electrode 12, and the electrodes 11 and 15 equally to the right and left of the electrode 13. The spacings are such that the line joining the mid-point of the line joining the electrodes 10 and 12 with the mid-point of the line joining the electrodes 11 and 13 passes just to the right of the heart outline and a similar line with respect to the electrodes 12 and 14, 13 and 15 passes just on the left of the heart outline. The heart is thus mainly contained within a rectangular outline 16 hereinafter referred to as the measurement zone.

Figure 2:
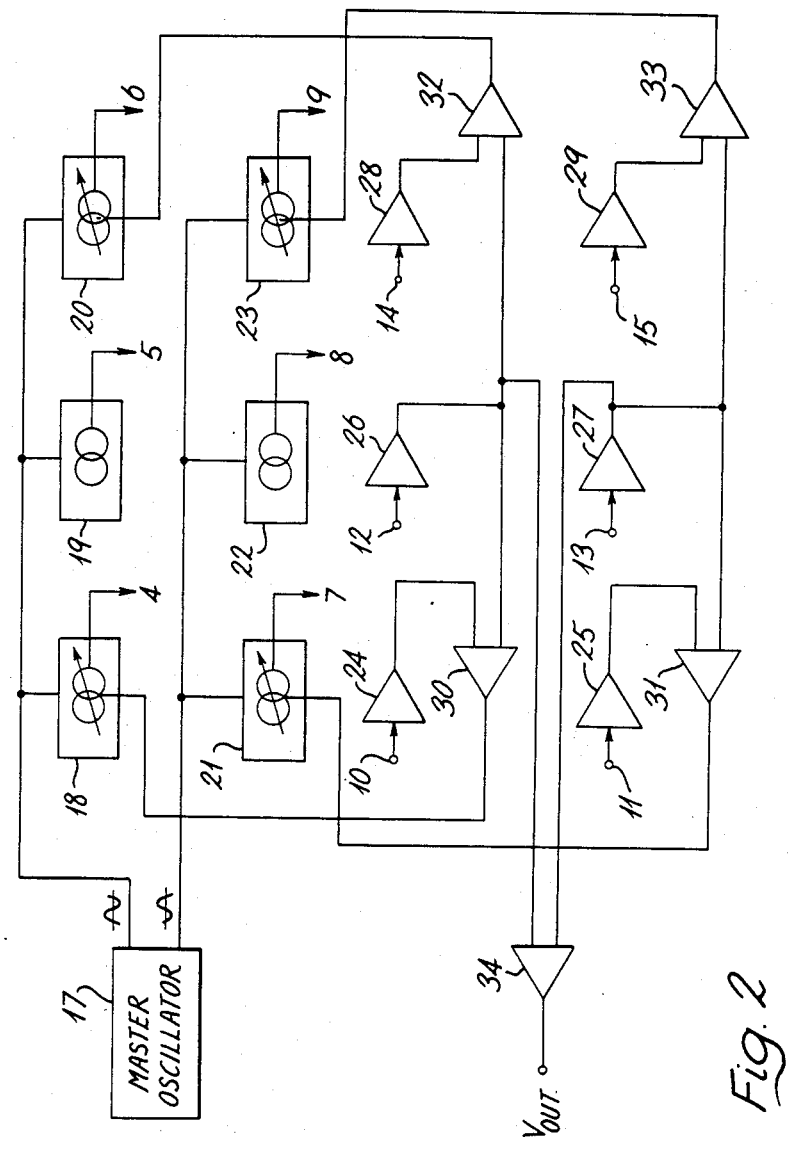
FIG. 2 is a block diagram of a circuit to be connected to the electrodes of FIG. 1.

A master oscillator 17 (shown in FIG. 2) drives six isolated constant current generators 18 to 23 from antiphase outputs such that the outputs of the generators 18, 19 and 20 connected to the electrodes 4, 5 and 6, respectively, are opposite in sign to those from the generators 21, 22 and 23 which are connected to the electrodes 7, 8 and 9, respectively.

Six high impedance buffer amplifiers 24 to 29 amplify the potentials at electrodes 10 to 15, which are then combined by means of difference amplifiers 30 to 34 which each incorporate rectification and filtering so that each amplifier has a d.c. output signal of magnitude and sign representing the difference between its input signals. Thus the potentials of the electrodes 10 and 12 are passed to buffer amplifiers 24 and 26 respectively and the difference between these potentials is obtained in the difference amplifier 30. The output from the amplifier 30 is used to control the output of the current generator 18 to the electrode 4 so that the potential difference of the electrode 10 is adjusted by changing the current through the impedance between the electrodes 4 and 10 to reduce the potential difference between the electrodes 10 and 12. Any difference between the potentials at the electrodes 11 and 13 is reduced to substantially zero by current from the generator 21 which is under the control of the difference amplifier 31 which in turn receives inputs from the buffers 25 and 27. Similarly any potential differences between the electrodes 12 and 14 and 13 and 15 are reduced to substantially zero by controlling the generators 20 and 23, respectively, by way of respective difference amplifiers 32 and 33 receiving inputs from the pairs of buffers 26, 28 and 27, 29. The output currents of the generators 19 and 22 passing by way of the electrodes 5 and 8 are held constant and in order to provide an indication of the impedance of the zone 16 containing the heart 2 the voltage between the electrodes 12 and 13 is measured. If an absolute measurement of impedance is required the voltage so obtained may be divided by a current passing between these electrodes. The required voltage is taken at the output from a difference amplifier 34 while a series milliametere between the generator 19 and the electrode 5 can be used to measure the current passing through the zone 16.

By keeping the electrodes 10 and 12 at substantially the same potential a portion of a virtual barrier as hereinbefore defined occurs at a point approximately halfway between the electrodes and a similar portion of a virtual barrier occurs between the electrodes 11 and 13 for the same reason. In effect a virtual barrier is set up along the left-hand boundary of the zone 16 as seen in FIG. 1. Thus current passing into the zone 16 through the top of the zone will tend to stay inside the zone. In addition when the impedance of the heart changes, for example when a comparatively large quantity of blood flows from the heart into the lungs, the boundary defined by the virtual barrier between the electrodes 10 and 12, and 11 and 13 is controlled to remain in the same position by adjustment of the currents flowing at the electrodes 4 and 7. In a similar way the right-hand boundary of the zone 16 is controlled by keeping the virtual barrier between the electrodes 12 and 14 and that between the electrodes 13 and 15 in a stable position by adjusting the currents at the electrodes 6 and 9. Thus the volume of the zone 16 will remain approximately constant and a measurement of its impedance variation with time and therefore with blood content can be measured. Measurement of the variations in the impedance of the zone 16 and therefore the heart 2 can be used to derive the stroke-volume of the heart and the cardiac output waveform.

The current generators 18 to 23 may each be integrated circuits type LM 13600 (manufactured by National Semiconductors). These circuits are transconductance amplifiers which each receive one input from the master oscillator 17 which can be regarded as setting the amplitude of a current provided by the circuit. The generators 18, 20, 21 and 23 also receive control inputs which in a transconductance amplifier form a product with the other inputs and thus vary the amplitude of the output current.

In an alternative control circuit the pairs of electrodes 10, 11; 12, 13 and 14, 15 are connected by way of respective buffer amplifiers as inputs to first, second and third difference amplifiers, respectively. The outputs of the first and second difference amplifiers are connected as inputs to a further difference amplifier with output connected to control the current through the electrodes 4 and 7, while the outputs of the second and third difference amplifier are connected as inputs to another further difference amplifier to control the current through the electrodes 6 and 9.

By keeping the potential difference between each outer pair of potential sensing electrodes (for example 10 and 11) equal to that between the inner electrodes 12 and 13 virtual barriers are set up along the vertical dotted lines of FIG. 1.

The arrangement of FIG. 1 has advantages in that it requires a relatively small number of electrodes to be applied to the body and these electrodes can be applied reasonably conveniently. However, since control is carried out from one surface of the body only, the results obtained cannot be expected to be as accurate as those obtained with an arrangement partly shown in FIGS. 3 and 4 where more electrodes are used and electrodes are applied to the back and front of the body.

Nine current input electrodes 35, 36, 37, 38, 39, 40, 41, 42 and 43 (see FIG. 3) of an array are shown applied to the front of the body. Between the electrodes 36 and 39, lie electrodes 44 and 45 for the determination of potential and potential differences. Other similar electrode pairs 46 and 47; 48 and 49; 50 and 51 lie on the lines from electrode 39 to the electrodes 38, 42 and 40 respectively. Electrode 39 is centred over the heart. A similar array is placed on the back of the body opposite the first. Currents enter by the front array and leave by the electrodes of the rear array. A zone 52 from front to back with approximately square cross-section is formed containing most of the heart. The shape of this zone may be varied by adjusting the positions of the corner electrodes 35, 37, 41 and 42.

A master oscillator 62 drives nine isolated constant current generators 53 to 61 in the same phase which are connected to the electrodes 35 to 43 of the front array. The oscillator 62 also drives a similar set of nine generators which are connected to electrodes of the rear array, the front and rear arrays being driven in antiphase. Eight high impedance buffer amplifiers 64 to 71 are coupled to the electrodes 44 to 51, respectively, of the front array, and similar buffer amplifiers are coupled to corresponding electrodes in the rear array. The potential difference between the electrodes 44 and 45 is determined by a difference amplifier 72; similarly the potential differences between the electrodes 46 and 47; 48 and 49 and 50 and 51 are determined by difference amplifiers 73, 74 and 75, respectively. The output of the amplifier 72 controls the current supplied by the generator 54 to electrode 36 in such a way that the potential difference between the electrodes 44 and 45 is reduced. The amplifiers 73, 74, 75 act similarly on generators 56, 60, 58 to control currents supplied to the electrodes 38, 42, 40 respectively. The outputs of amplifiers 72 and 73 are summed in a summing amplifier 76 which in turn controls the current supplied by generator 53 to the corner electrode 35. Summing amplifiers 77, 78, 79 control the generators 59, 61, 55 in a similar way to supply the other three corner electrodes 41, 43, 57 respectively. An amplifier 80 sums the output of the four buffer amplifiers 65, 67, 69, 71 to produce an output proportional to the mean potential of the electrodes 45, 47, 49 and 51 surrounding the primary current electrode 39. A similar circuit is connected to the electrodes of the rear array. An amplifier 81 determines the potential difference between the front and rear surfaces of the measurement zone 52 by differencing the outputs of the amplifier 80 and of a similar amplifier connected to the rear array. The output of amplifier 81 is proportional to the impedance of the measurement zone since the current through the zone is constant.

Figure 12:
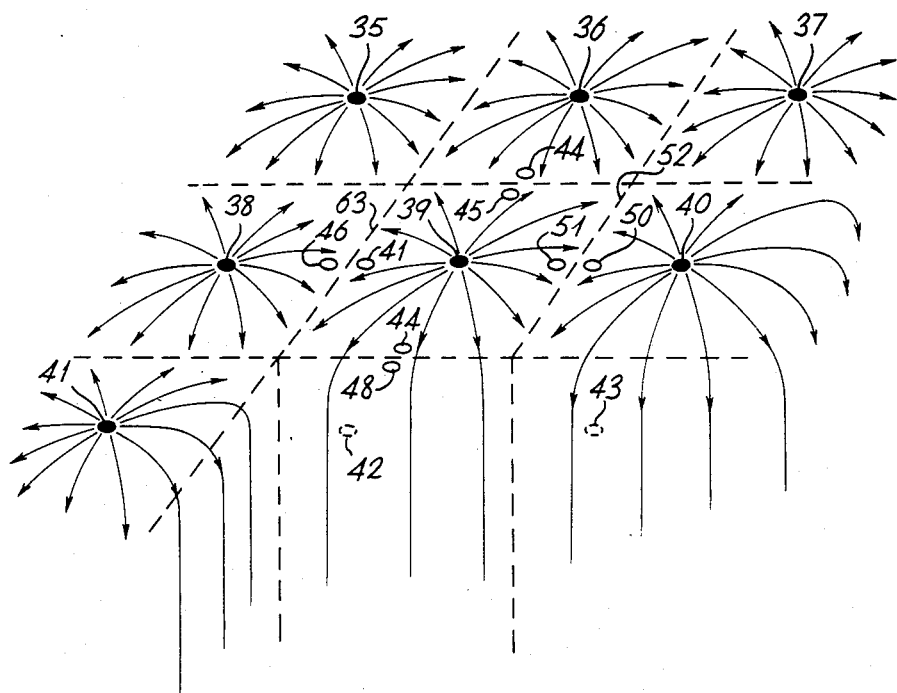
FIG. 12 is a schematic view of current patterns set up by the electrodes of FIG. 3.

In order to illustrate the operation of the invention a three dimensional view of the currents from the front array when this array is positive is shown in FIG. 12. The front array is shown horizontal and only currents flowing within the rectangle defined by the electrodes 35, 37, 41 and 43 appear. As a result of the layout of the electrodes of the front and rear arrays a virtual barrier in the form of a plane with edge indicated by the dashed line 63 is set up between the electrodes 36 and 39 and the corresponding electrodes in the rear array. By keeping the potential difference between the electrodes 44 and 45, and between the corresponding electrodes substantially at zero, this virtual barrier is kept in the position shown regardless of how the impedance of the zone 52 changes. The pairs of electrodes 46 and 47, 48 and 59 and 50 and 51 have the same effect on virtual boundaries forming other edges of the zone 52. Control signals derived by differencing the potentials at the electrodes 44 and 45, and 46 and 47 control a current passed through the electrode 45 to keep the top left corner of the zone 52 in approximately the position indicated. Similar control signals for the currents passed through the electrodes 37, 41 and 43 keep the other "corners" in constant positions. The zone 52 need not, and in practice is not, of the perfect rectangular shape shown but provided its outline remains reasonably constant impedance measurements of the heart can be made. For this purpose the output voltage of the amplifier 81 may be divided by a constant current passed through the electrode 39 and the corresponding electrode of the rear array.

Figure 5:
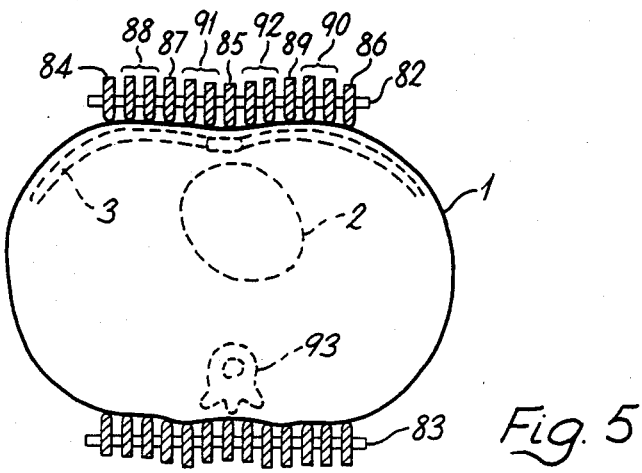

Front and rear arrays of electrodes (see FIGS. 5 and 6) may be used for generating a trans-thoracic impedance map of the body The body is represented in outline at 1, the heart at 2 and the ribs at 3. A central row of electrodes forming part of an array 82 are shown in section all touching the skin as are a row of electrodes in a second array 83 at the rear. In a practical arrangement each electrode is spring loaded perpendicular to the plane of the array so that contact is established with the irregularly shaped human body. The electrodes 84 and 86 at either end of the row are control current electrodes, passing currents which are controlled but not measured; whilst the group 85, 87 and 89 in the centre are measurement current electrodes, passing currents which are measured and, except for the electrode 85, controlled. Interposed between each pair of current electrodes are pairs of potential sensing electrodes 88, 90, 91 and 92.

Figure 6:
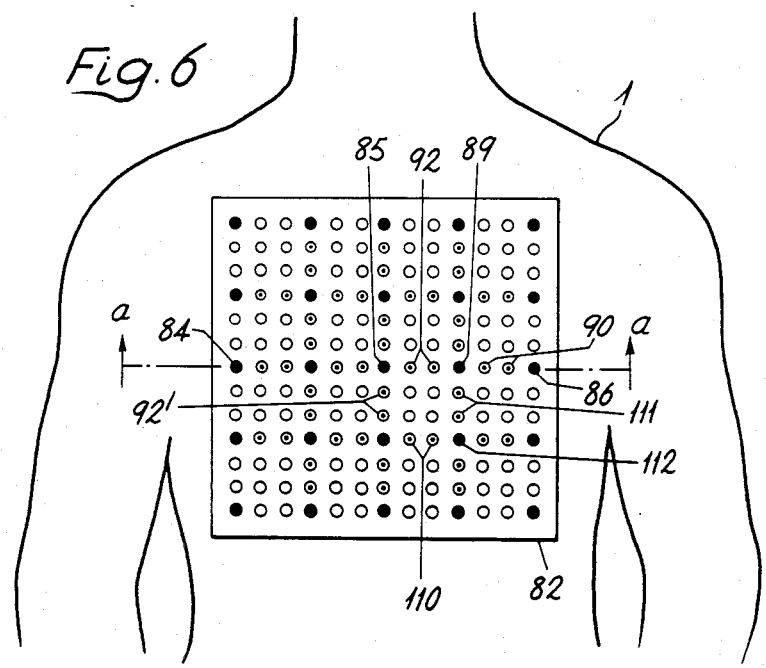

FIG. 6 shows the array 82 consisting of several similar rows of electrodes lying on either side of the central row. Every third row except the outermost rows is constituted as described above, although in this instance only one such row on either side of the central row is shown. The two intermediate rows provide potential sensing pairs in every third column.

The outermost rows at the extreme ends of the array function as control current electrodes, current being supplied from every third electrode, and the intermediate electrodes being disconnected.

Figure 3:
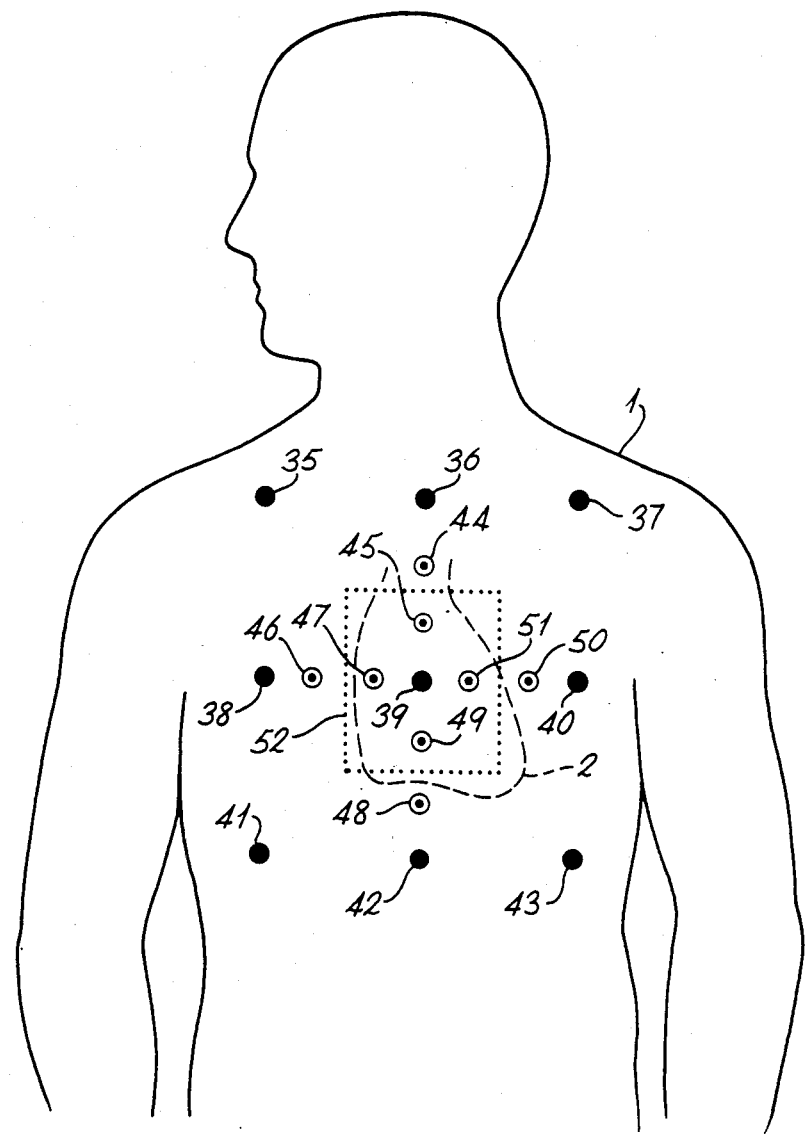
FIG. 3 shows the layout of electrodes for use in determining the impedance of the heart.
Figure 4:
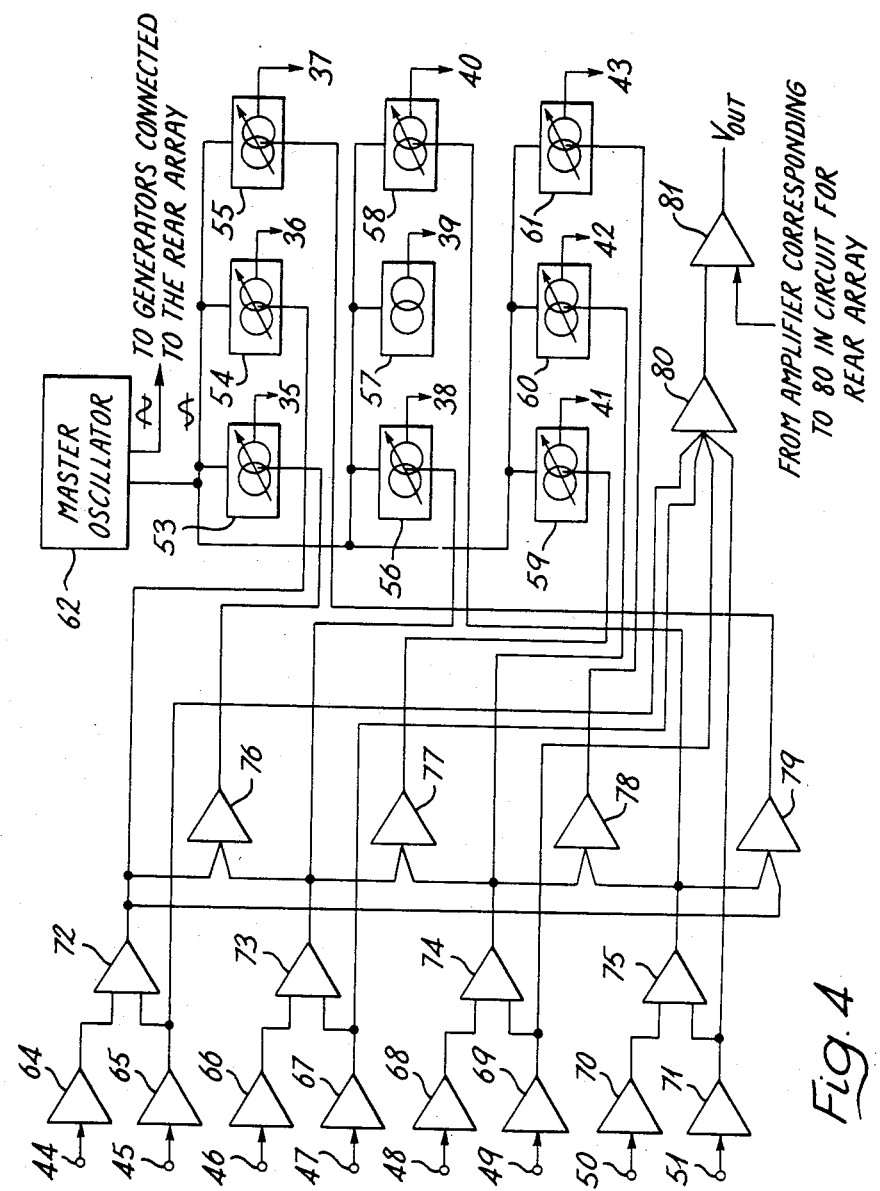
FIG. 4 is a block diagram of a circuit to be connected to the electrodes of FIG. 3, FIGS. 5 and 6 show arrays of electrodes for application to the human body with FIG. 5 showing a cross-section on the line a—a through front and rear arrays and the body (excluding the arms)

Current generators, buffer amplifiers and difference amplifiers are provided in a circuit (not shown) according to the same principle of interconnection illustrated in FIGS. 3 and 4. For example the electrode 85 is connected to a constant current generator which, during measurements, supplies a constant current and the electrode pair 92 is connected by way of respective buffers to a difference amplifier whose output controls a constant current generator supplying current to the electrode 89. Similarly the potential difference between the electrodes 90 is used to control the current supplied by the electrode 86. Working out from the central electrode 85 in each direction each electrode in the row "aa" is connected according to the same principle as are the electrodes in the column at right angles thereto. Current electrodes on diagonals through the electrode 85 are each controlled by four current measuring electrodes; for example pairs of potential sensing electrodes 110 and 111 are connected by way of buffer amplifiers to respective difference amplifiers and the outputs of these difference amplifiers are summed by a summing amplifier whose output is used to control current passing by way of a current electrode 112. Alternatively the potential differences between the electrodes 92 and electrodes 92' may be used to control current through the electrode 112 and this principle is used for the corner electrodes of the array.

In order to measure the impedance of a zone centred on the electrode 85 and the corresponding electrode in the rear array, and extending approximately as far as boundaries running between the pair of electrodes 92 and corresponding potential sensing electrodes adjacent to the electrode 85, the potentials of the four potential sensing electrodes adjacent to the electrode 85 are averaged, or summed, and divided by the current passing by way of the electrode 85. Summing may be carried out by connecting the four electrodes by way of their buffer amplifiers to a summing amplifier. The same process may be carried out for every zone centred on a current measuring electrode but not the current control electrodes in the outer rows and columns. In order to avoid duplication of summing amplifiers and measuring circuits, a multiplexing arrangement, controlled by a microcomputer may be used. Further multiplexing may be employed to allow electrodes to have different functions at different times. For example if all positions in the array are fitted with electrodes the pattern shown in FIG. 6 may be moved one row to the left, or right, or up or down so that the measurement zones are centred slightly differently. Further the front and back arrays can be switched at different times. Data collected by a microcomputer can then be used to print a map or can be processed to provide different types of display.

Current through any of the current carrying electrodes except the electrode 85 may be controlled according to the expression:

$$\frac{P_{nm}}{S_{nm}} = \frac{P_{(n+1)m}}{S_{(n+1)m}}$$

where

P is potential,

S is distance through the body between corresponding electrodes in the front and rear arrays, and n and m are subscripts representing positions in rows and columns, respectively, with the position of the electrode 85 as datum for both n and m.

Apparatus which can be used for collecting multiangular data from which a tomographic image of the human body may be formed is shown in FIGS. 7 to 11 and is now described. Similar apparatus for animal, plant or inanimate bodies may be made according to the invention.

Figure 7:
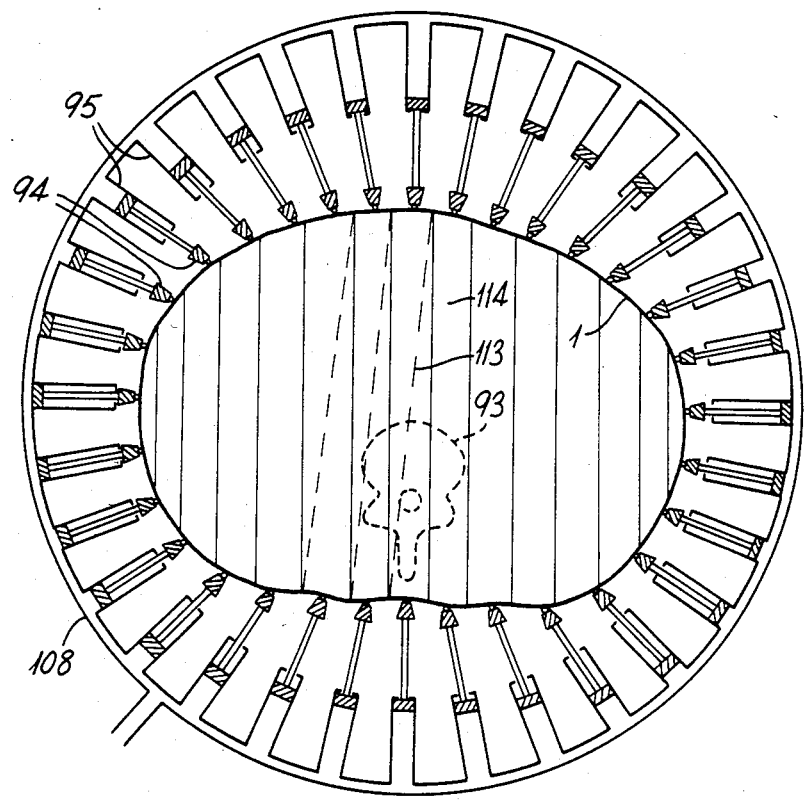
FIG. 7 shows an array of electrode holders for use in tomographic imaging of a body section, FIGS. 8 to 11 give details of the electrode holders and electrodes for use with the arrangement of FIG. 7.
Figure 11:
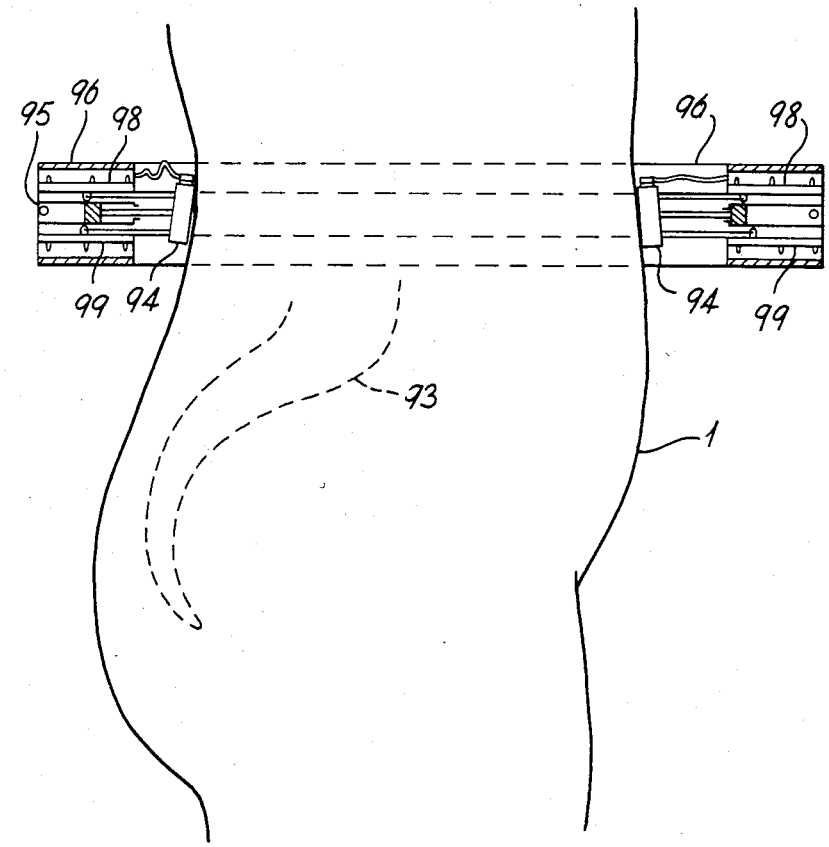

In FIG. 7 the body is represented in cross-section at 1, the spine at 93. A single encircling set of for example, thirty-two electrode holders 94 are shown in section all touching the skin. The number of electrode holders is a compromise since better results in terms of discrimination will be obtained the closer the number of electrodes tends to infinity but magnitude and complexity of associated circuitry increase rapidly with increase in the number of electrodes.

Each electrode holder is mounted on a pneumatic or hydraulic cylinder 95 which is connected to a common pressure line 108. When pressure is applied the electrode holders advance until the skin is contacted and the contact pressure is then constant at all contact points around the body. The electrode holders are mounted in a circular yoke 96 (FIG. 11) which may be opened to admit the patient. Coupled to the individual electrode holders are means 98, 99 such as potentiometers (see FIG. 9) whereby the position of the holder on a radius of the yoke and its tilt may be determined.

In FIGS. 9 and 10, electrodes 101 and 103 form current control electrodes while an electrode 102 is a current measurement electrode. Electrodes 104, 105, 106 and 107 are potential sensing electrodes connected to control the currents from the electrodes 101 and 102. All electrodes are spring loaded to ensure good contact with the body in spite of local irregularities in shape.

Current control defining the zones shown by the lines within the body 1 in FIG. 7 is carried out as described below. In a single holder the potential difference between the electrodes 104 and 105 controls the current from the electrode 101 and that between the electrodes 106 and 107 controls the current from the electrode 103. The currents through the electrodes 102 in the holders at the ends of a central zone 113 are of constant amplitude but the currents in the electrodes 102 at the ends of an adjacent zone 114 are controlled by a signal which depends on the potential differences at the electrodes 105 or 106 of the same holder and the adjacent holder. In this way the amplitudes of currents from the central electrodes of each holder are controlled working out from the centre zone 113 to the extreme zones.

Ideally if the body were homogeneous each of the zones shown within the body in FIG. 7 would carry an equal current density. Where equally angularly spaced electrodes are used, if currents supplied to electrodes furthest from the central axis equal those supplied to electrodes nearer the axis, then there is an excess of current near the periphery and current flow lines bow towards the centre. Equality of current density in each zone can be obtained when the current supplied is proportional to effective zone width; that is $$I_n = I_o \left[ \frac{r_{n+1}\sin\theta_{(n+1)} - r_{n-1}\sin\theta_{(n-1)}}{r_1\sin\theta_1 - r_{(-1)}\sin\theta_{(-1)}} \right] \quad \text{equation 1}$$

where $I_o$ is the current passing through the central zone, n is the number of electrode holders with n=0 for the electrode holders of the central zone, $$r_n = R - d_n$$

R = the radius of the ring formed when all electrodes have zero displacement towards the centre of the body, $d_n$ = is the displacement of the $n^{th}$ holder towards the centre of the body, $r_{(-1)}$ = the value of $r_n$ for the zone on the opposite side of the central zone from the zone with value $r_1$, and $\theta_n$ is the angle between the radii passing through the electrodes corresponding to n=0 and n.

Thus each electrode 102 is supplied according to equation 1 although for electrodes not contacting the central zone a further modification is carried out as is described below.

Figure 14:
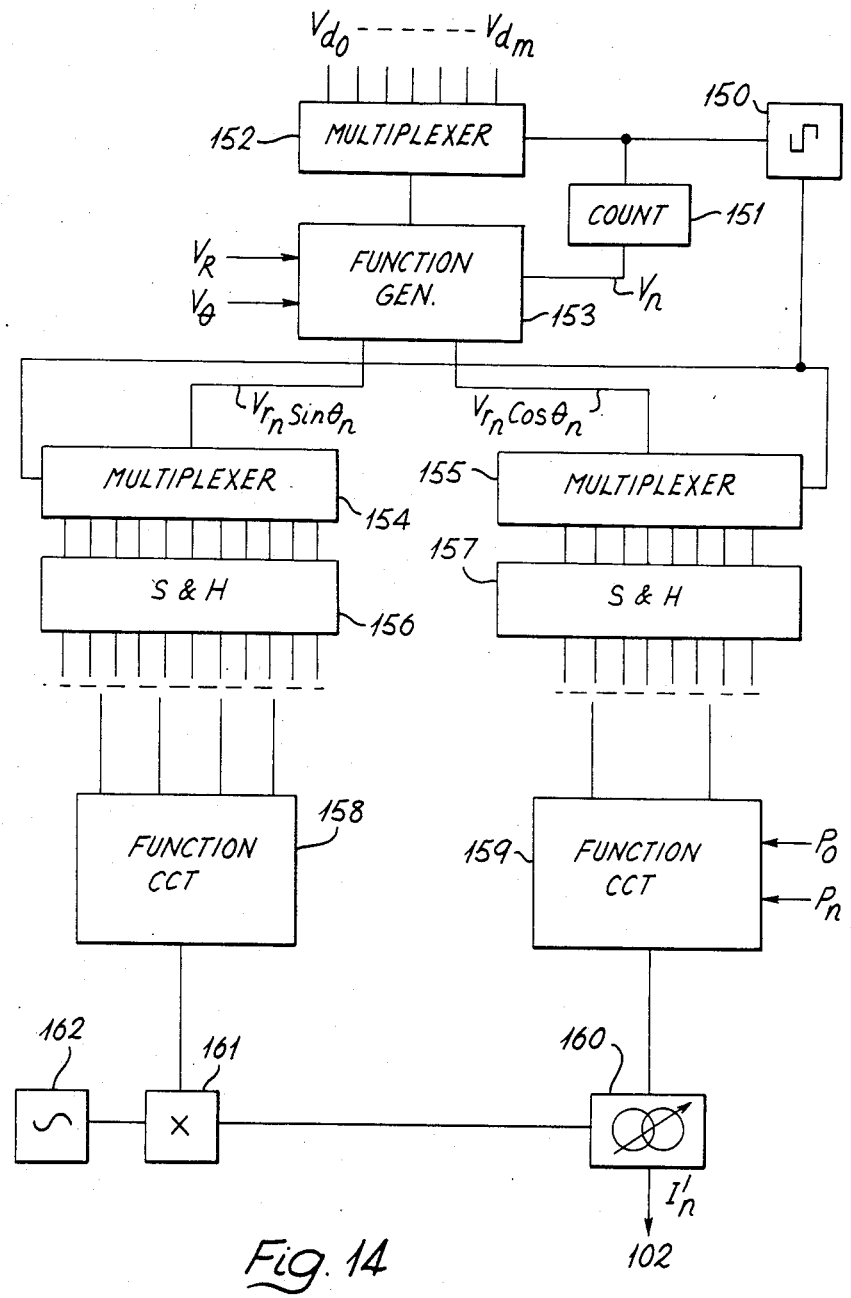
FIG. 14 is a block diagram of part of a circuit for supplying currents to the electrodes of the holders of FIGS. 7 to 11, and FIGS. 15 and 16 show details of the circuit of FIG. 14.

In FIG. 14 a clocking oscillator 150 drives a counter 151 to produce an output n indicative of its state and a multiplexer 152 to sample the outputs Vdn of the position sensors 98 (or 99). The values n and Vdn are combined with fixed values $V_R$ and $V_{\theta 1}$ in the vector function generator 153 which is reset by the counter 151 after a count of n. $V_R$ and $V_{\theta 1}$ are fixed voltages with $V_R$ proportional to the radius of the yoke and having the same constant of proportionality as Vdn. Each set of input values produces at the output signals corresponding to $r_n \cos \theta_n$ and $r_n \sin \theta_n$, and multiplexers 154 and 155 couple the outputs to sample and hold stages 156 and 157 which enable values of $r_n \sin \theta_n$ and $r_n \cos \theta_n$ to be obtained simultaneously for all allowable values of n.

A zone width function circuit 158 combines four outputs from the stored values of $r_n \sin \theta_n$ to give $$\frac{r_{n+1}\sin\theta_{(n+1)} - r_{n-1}\sin\theta_{(n-1)}}{(r_1 + r_{-1})\sin\theta}$$

which is applied to one input of multiplier 161. The other input is supplied by a master oscillator 162 which operates at 10 kHz. The output connects to the carrier input terminal of current generator 160 with output connected to one of the electrodes 102.

In order to set up horizontal virtual barriers, the potential difference between the electrodes 104 and 105 of each holder controls the current from the electrode 101 of that holder, and the potential difference between the electrodes 106 and 107 controls the current from the electrode 103. The electrodes 101 and 103 are coupled to current generators (not shown) receiving one input from the oscillator 150 and one representative of the control signal derived as described.

In a homogenous object the uniform current distribution described would produce a potential difference between the ends of a zone proportional to the length of that zone. So that if the object were circular in cross section the potential at any point P on the surface would be given by $P_o r \cos \theta$, $P_o$ being the potential at the end of the central zone.

In the proposed apparatus where there is a maximum radius R, which can be accommodated and the potentials are measured at fixed angular increments round a common centre, the relationship may be expressed as $$P_n = P_o(R - d_n)\cos \theta$$

$P_o$ is the potential at the end of the central zone.

According to the invention current supplied is modified to compensate for differences in impedance arising from variations in homogeneity between one zone and the next. Suitable control signals are generated by a potential difference function circuit 159 combining two outputs from the stored values of $r_n \cos \theta_n$ with potentials $P_o$ and $P_n$ from the electrodes 105 of the same holder containing that electrode 102 and of an adjacent holder to give $$\frac{P_o}{r_o} - \frac{P_n}{r_n \cos\theta_n}$$

which is connected to the control input on current generator 160. The output from generator 160 is applied to the $n^{th}$ electrode of type 102 and, of course, there is one generator 160 for each electrode 102.

Since there may be variations in shape of the body perpendicular to the plane of measurement, a difference signal dependent on the signals from the potentiometer 98 and 99, indicative of the tilt of the holder may also be used as a correction.

Figure 15:
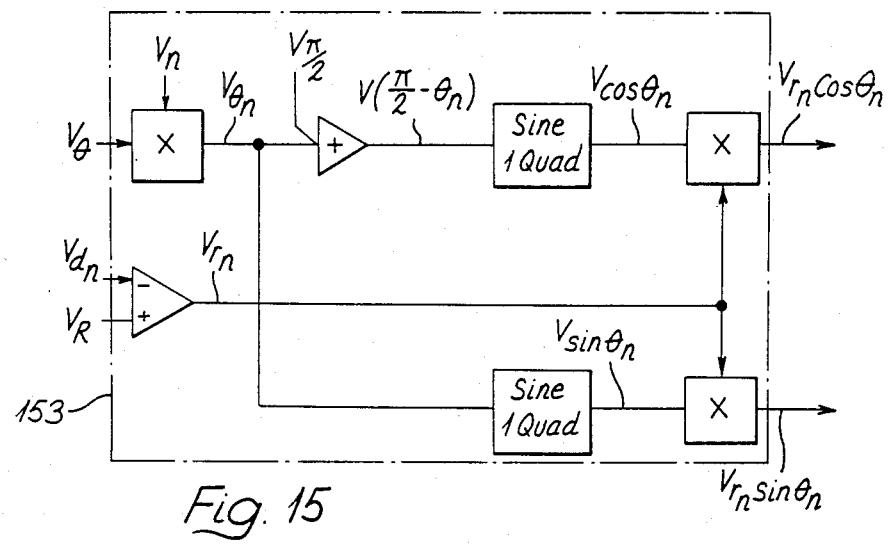
Figure 16:
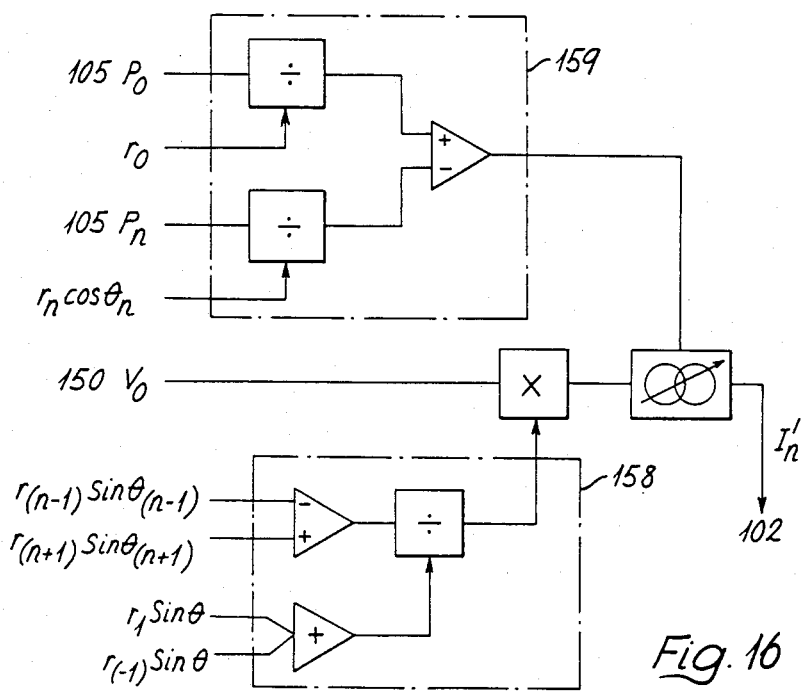

The function generator 153 may be based on the Burr Brown multifunction convertor type 4302. Data sheets for this device explain how sin and cosine functions may be derived. FIGS. 15 and 16 show details of the generator 153, and the circuits 158 and 159.

Currents are passed through each zone using electrodes which are energised in phase opposition in two holders but the electrodes lying on the diameter perpendicular to direction of main current flow are not energised. Thus each zone passes current at the same time and its relative impedance may be calculated, for example, using a microcomputer multiplexed to divide the potential difference between the means potentials at the electrodes 105 and 106 at holders at each end of each zone by the current between electrodes 102 of that zone.

With the control arrangement described the control signals applied to the current generators 160 are proportional to the differences in the relative admittivities of the zones, and consequently an admittivity distribution can be calculated without measurement of current values in all zones.

Figure 13:
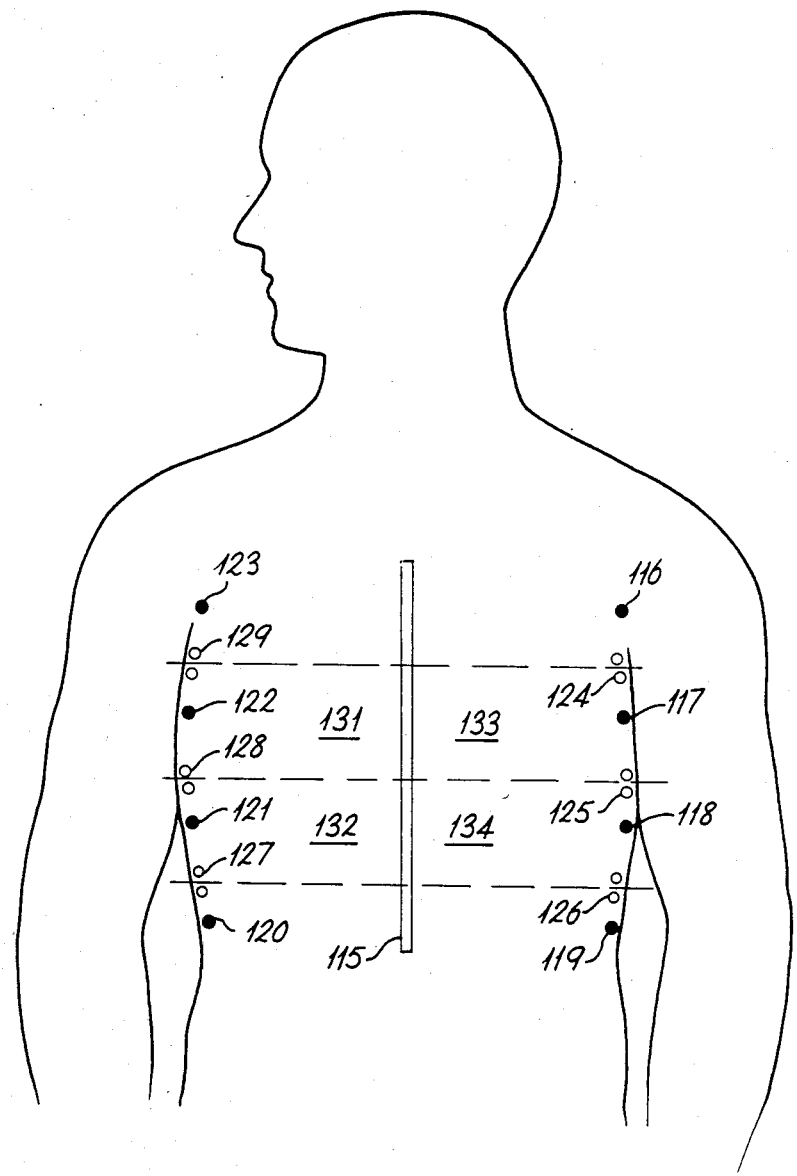
FIG. 13 shows an arrangement of electrodes for measuring the impedance of zones of the lungs.

Having made such measurements for one set of zones the connections to the electrodes are switched so that the central zone 113 moves one position, for example, clockwise, and so on until each "diameter" of the thorax has formed the central zone 113. In order to gain additional information zones which are based on a central zone which is not "diametric" may be employed as shown by the dashed lines in FIG. 7, only two such zones being shown for the sake of clarity. In this way a large amount of data can be built up from which a tomographic image may be formed.

Where it is required to make measurements of impedance relating to the lungs the arrangement shown in FIG. 13 may be used. A strip electrode 115 is fixed along the line of the sternum and a similar electrode is fixed along the line of the backbone. Eight current electrodes 116 to 123 are fixed on the sides of the body together with six pairs of potential sensing electrodes 124 to 129 positioned between the current electrodes. A current of constant amplitude is passed through the electrode 122 to the electrode 115 and the corresponding electrode on the back. Similarly a constant amplitude current is passed through the electrode 117 and controlled currents are passed through the current electrodes 116 and 118 to 121 and 123, control being derived from the potential difference of respective adjacent pairs of potential sensing electrodes working outwards from the electrodes 122 and 117. In this way the chest is divided into zones 131 to 134, having boundaries indicated by the chain dotted lines shown in FIG. 13 and the electrode 115. Measurement of the current through the electrode 122 and the potential between the electrode 128 and the electrode 115 (or the corresponding electrode on the back) provides the impedance of the zone 131 and the impedances of the other zones are found in a similar way.

In another arrangement the electrode 115 and the corresponding electrode may be replaced by pairs of current electrodes situated along the zone boundaries on either side of the centre line of the chest.

When in the above described embodiments of the invention, the potential sensing electrodes are in pairs close together, the resulting virtual barriers are well defined and consequently, the position of the division between zones is precisely known. However, the potential electrodes are then well spaced from the current electrodes and there is a region between the current electrode ad the equipotential on which the potential electrodes lie, which is not included in the zone impedance calculation. This introduces an error or end correction.

On the other hand, if a potential sensing electrode is located close to, or concentric with, the current source electrode, it measures the potential near that electrode. The spacing between the potential electrodes in adjacent zones is increased so that the zone boundaries are less precisely defined.

A reasonable compromise which allows for interchange of electrode function is to have all electrodes equally spaced and of the same size. However, circumstances often arise in using the invention in which concentric electrodes are useful.

Many other ways of putting the invention into effect than those specifically described will now be apparent. For example different arrangements of electrodes can be used to isolate different parts of the body and it will be clear that the invention can be employed in determining the internal impedances of other objects, for example for the detection of voids in tree trunks or the detection of solid or gas entrainment in piped liquids. Use of the invention is not limited to relatively small objects but may be used anywhere where it is required to isolate a portion of a body for impedance measurements, provided that electrodes can be placed near the portion whose impedance is required. The currents in all zones may be controllably variable, for example in accordance with potentials relating to the positions of potential minima, since it is not necessary that the current in one zone is of constant amplitude.

I claim:

1. Medical investigative apparatus for deriving signals representative of the impedance of a zone of an animal body, comprising means for passing first currents between electrodes of a first group suitable for location on at least one surface of an animal body, the electrodes being, in operation, positioned to pass the first currents through the zone whose irpedance is to be measured, means for deriving the potential difference across the zone due to the first currents and substantially in the direction of the said first currents, means for passing second currents through the body between electrodes of a second group also suitable for location on at least one surface of the body to establish virtual barriers generally coinciding with boundaries of the zone within the body, a said virtual barrier being formed along a said boundary when there is no potential gradient in the body perpendicular to the boundary and maximum potential gradient along the boundary, means for deriving from potentials in the body control signals representative of the positions of the said virtual barriers, and means for controlling the second currents in accordance with the control signals to control the positions of the said virtual barriers, the potential difference across the zone being representative of the impedance of the zone.

2. Apparatus according to claim 1 wherein the means for deriving potential difference comprises a plurality of potential sensing electrodes connected to respective high input-impedance amplification means, the potential sensing electrodes being, in operation, positioned in pairs, one on each side of a said virtual barrier, and the means for deriving control signals derives signals representative of the potential differences between electrodes of each pair.

3. Apparatus according to claim 2 wherein each electrode in the first and second groups is connected to a constant alternating-current generator, the generators connected to electrodes in the first group generating a constant amplitude output current, and the generators connected to electrodes in the second group gdnerating output currents with amplitudes which vary according to respective control signals.

4. Apparatus according to claim 2 for use in deriving the impedance of a generally rectangular zone comprising six sensing electrodes positioned on one surface of the body with one sensing electrode at each of opposite ends of the zone between two sensitive electrodes outside the zone but in line with each said end, the first group of electrodes comprising two current electrodes remote from the zone, the second group of electrodes corprising two pairs of current control electrodes, each pair being positioned to pass current outside the zone substantially parallel to the sides thereof and adjacent to two sensing electrodes in line with the opposite ends of the zone.

5. Apparatus according to claim 2 wherein the electrodes are positioned in two arrays each comprising electrodes in the first and second group and sensing electrodes, the arrays being adapted to be positioned on different surfaces of the body, and currents pass through the body from one surface to another.

6. Apparatus according to claim 5 for use in deriving the impedance of a zone which is generally rectangular in cross-section normal to current flow wherein each array comprises a central current electrode which forms a part of the first group of electrodes, eight current control electrodes forming part of the second group of electrodes, the current electrodes forming a rectangular three-by-three array centered on one end of the zone, and four pairs of sensing electrodes, each pair being located in a row or column of the three-by-three array adjacent to the central current electrode, the means for deriving control signals deriving first difference signals from each pair of sensing electrodes to control the current supplied by that one of the said control current electrodes which is external to that pair in the array and in the same row or column, and deriving sum signals from each pair of first difference signals derived from adjacent pairs of sensing electrodes to control the current supplied by current control electrodes at that corner of the three-by-three array which is adjacent to those pairs of sensing electrodes.

7. Apparatus according to claim 5 for use in deriving the impedances of a plurality of zones which are generally rectangular in cross-section normal to current flow, wherein each array is rectangular and comprises a central current electrode which forms part of the first group of electrodes, rows and columns of control current electrodes which form part of the second group of electrodes, and sensing electrodes between the current electrodes in the rows and columns, the seans for deriving control signals deriving a respective control signal to control the current supplied by each control current electrode from sensing electrodes in a region adjacent to, and inward of, that control current electrode in the array, and the current supplied by each current electrode and a potential derived from at least one of the sensing electrodes adjacent to that current electrode being the current and potential representative of the impedance of a zone centred on that current electrode.

8. Apparatus according to claim 7 wherein the means for deriving control signals derives control signals representative of the value:

$$\frac{P_n}{S_n} - \frac{P_{n+1}}{S_{n+1}}$$

where $P_n$ is the potential at the $n^{th}$ sensing electrode from the center of a row or column and $S_n$ is the distance through the body from the $n^{th}$ electrode in one array to the corresponding electrode in the other array.

9. Apparatus according to claim 1 wherein the first and second groups of electrodes include an electrode common to both groups and except for the cormon electrode, each electrode in the first and second groups is connected to a constant alternating-current generator, the generators connected to electrodes in the first group generating a constant amplitude output current, and the generators connected to electrodes in the second group generating output currents with amplitudes which vary according to respective control signals.

10. Apparatus according to claim 9 for deriving current and potential signals representative of the impedances of zones of the human body containing significant portions of the lungs, comprising two common electrodes one located over the sternum and one located over the spine, a plurality of current electrodes spaced apart along the sides of the body in the region of the chest, with sensing electrodes between the current electrodes, one current electrode on each side of the body being in the first group of electrodes, the other current electrodes being in the second group, and the current in each electrode in the second group being controlled by the potential difference between sensing electrodes adjacent thereto but on that side thereof adjacent to the nearest electrode in the first group.

11. Apparatus for deriving signals representative of the impedance of a zone of a cross-section of a closed body, comprising an assembly including a supporting member, a plurality of electrode holders mounted thereon, the supporting member being arranged to encircle, in operation, a portion of the human body, and electrodes held by the said holders, the said holders being adapted to hold the said electrodes in contact with the surface of the said body, means for passing first currents between a plurality of the electrodes in a first group positioned to pass the first currents through the zone whose impedance is to be measured, means for deriving the potential difference across the zone due to the first currents and substantially in the direction of the said first currents, means for passing currents through the body between a plurality of the electrodes in a second group positioned in relation to electrodes of the first group to establish virtual barriers generally coinciding with boundaries of the zone within the body, a said virtual barrier being formed along a said boundary when there is no potential gradient in the body perpendicular to the boundary and maximum potential gradient along the boundary, means for deriving from potentials in the body control signals representative of the positions of the potential barriers, and means for controlling the second currents in accordance with the control signals to control the positions of the potential barriers, the potential difference across the zone being representative of the impedance of the zone.

12. Apparatus according to claim 11 wherein the means for deriving potential difference comprises a plurality of potential sensing electrodes connected to respective high input-impedance amplification means, the potential sensing electrodes being, in operation, positioned in pairs, one on each side of a said virtual barrier, and the means for deriving control signals derives signals representative of the potential differences between electrodes of each pair.

13. Apparatus according to claim 12 wherein each electrode in the first and second groups is connected to a constant alternating-current generator, generators connected to electrodes in the first group generating a constant amplitude output current, and generators connected to electrodes in the second group generating output currents with amplitudes which vary according to respective control signals.

14. Apparatus according to Claim 2 comprising means for applying forces to the holders automatically to cause the holders to press on to the body with equal contact pressure.

15. Apparatus according to claim 11 including means for generating respective signals representative of the displacements of each electrode from a circular datum.

16. Apparatus according to claim 11 including means for generating respective signals representative of the inclinations of the holders from the perpendicular to the plane of encirclement of the electrode holders.

17. Apparatus according to claim 11 wherein the said zone passes through the center of a cross-section of the body, the apparatus including means for supplying one electrode in each holder with a current according to the expression:

$$I_n = I_o \left[ \frac{r_{n+1}\sin\theta_{(n+1)} - r_{n-1}\sin\theta_{(n-1)}}{r_1\sin\theta - r_{(-1)}\sin\theta_{(-1)}} \right]$$

where $I_o$ is the current passed between electrodes at the ends of said zone, n is the number of electrode holders with n=0 for the electrode holders of the central zone, $r_n = R - d_n$ R is the radius of the ring formed when all the electrode holders have zero displacement towards the center of the body, $d_n$ is the displacement of the $n^{th}$ holder towards the center of the body, $r_{(-1)}$ is the value of $r_n$ for zone on the opposite side of the central zone from the zone with the value $r_1$, and $\theta_n$ is the angle between the radii passing through the electrodes corresponding to n=0 and n.

18. Apparatus according to claim 11, wherein the means for deriving control signals derives control signals representative of the value:

$$\frac{P_n}{(R - d_n)\cos\theta_n} - \frac{P_{n+1}}{(R - d_{n+1})\cos\theta_{(n+1)}}$$

where n is the number of electrode holders with n=0 for the electrode holders of the central zone, R is the radius of the ring formed when all the electrode holders have zero displacement towards the center of the body, $P_n$ and $P_{n+1}$ are the potentials of sensing electrodes in the $n^{th}$ and $(n+1)^{th}$ holders, respectively, and $\theta_n$ is the angle between the radii passing through the electrodes corresponding to n=0 and n.

19. A method of deriving the impedance of a zone of a body using electrodes placed in contact with the body wherein the dimensions of the zone are comparable with the maximum distances between the electrodes, comprising positioning and energizing electrodes of a first group on the surface of the body to pass first currents through the zone, deriving the potential difference across the zone due to the first currents and substantially in the direction of the said first currents, positioning and energizing electrodes of a second group on the surface of the body to establish virtual barriers generally coinciding with boundaries of the zone within the body by passing control currents between the electrodes of the second group, a said virtual barrier being formed along a said boundary when there is no potential gradient in the body perpendicular to the boundary and maximum potential gradient along the boundary, adjusting the control currents in accordance with potentials representative of the positions of the virtual barriers to control the said positions, and deriving an indication of the impedance of the zone from the said potential difference across the zone.

* * * * *